(12) United States Patent
Teiwes et al.

(10) Patent No.: US 8,811,657 B2
(45) Date of Patent: Aug. 19, 2014

(54) METHOD AND APPARATUS FOR IMAGE-BASED EYE TRACKING FOR RETINAL DIAGNOSTIC OR SURGERY DEVICE

(75) Inventors: Winfried Teiwes, Teltow (DE); Horia Grecu, Teltow (DE)

(73) Assignee: OD-OS GmbH (DE)

( * ) Notice: Subject to any disclaimer, the term of this patent is extended or adjusted under 35 U.S.C. 154(b) by 1933 days.

(21) Appl. No.: 11/142,962

(22) Filed: Jun. 1, 2005

(65) Prior Publication Data

US 2005/0270486 A1    Dec. 8, 2005

(30) Foreign Application Priority Data

Jun. 2, 2004    (EP) ..................................... 04013015

(51) Int. Cl.
     *G06K 9/00* (2006.01)

(52) U.S. Cl.
     USPC ........... 382/103; 382/107; 382/128; 382/117; 382/181; 351/209; 351/239; 396/51; 128/922

(58) Field of Classification Search
     USPC .......... 351/209, 239; 382/181, 103, 107, 117, 382/128, 206, 195, 272; 396/51; 128/922
     See application file for complete search history.

(56) References Cited

U.S. PATENT DOCUMENTS

| | | | | |
|---|---|---|---|---|
| 5,557,350 | A * | 9/1996 | Yano | 351/208 |
| 5,865,832 | A | 2/1999 | Knopp et al. | 606/10 |
| 6,714,665 | B1 * | 3/2004 | Hanna et al. | 382/117 |
| 2002/0013577 | A1 * | 1/2002 | Frey et al. | 606/5 |
| 2002/0141614 | A1 | 10/2002 | Lin | 382/103 |
| 2003/0016850 | A1 * | 1/2003 | Kaufman et al. | 382/128 |
| 2003/0108220 | A1 * | 6/2003 | Jepson et al. | 382/103 |
| 2003/0199769 | A1 * | 10/2003 | Podoleanu et al. | 600/476 |
| 2003/0223037 | A1 * | 12/2003 | Chernyak | 351/209 |
| 2004/0146219 | A1 * | 7/2004 | Sathyanarayana | 382/300 |
| 2004/0263859 | A1 * | 12/2004 | Chang et al. | 356/497 |

FOREIGN PATENT DOCUMENTS

| | | | | |
|---|---|---|---|---|
| DE | 199 54 047 | | 5/2001 | |
| WO | WO 02/064031 | | 8/2002 | |
| WO | WO 02/064031 A2 | * | 8/2002 | A61B 3/113 |
| WO | WO 02064031 A2 | * | 8/2002 | A61B 3/113 |
| WO | WO 03/053228 | | 7/2003 | |

OTHER PUBLICATIONS

Ip, L.P.S.; Nguyen, T.Q.; Bartsch, D.-U.; Fundus based eye tracker for optical coherence tomography. Engineering in Medicine and Biology Society, 2004. IEMBS '04. 26th Annual International Conference of the IEEE 2004 pp. 1505-1508 vol. 2.*

Bradski, Gary; Computer Vision Face Tracking for Use in a Perceptual User Interface. Microcomputer Research Lab, Intel Technology Journal Q2 1998, pp. 1-15.*

Morimoto, C.H., et al. "Pupil detection and tracking using multiple light sources." Image and Vision Computing vol. 18, Issue 4, Mar. 1, 2000, pp. 331-335.*

"Interpolate." Def. 1 & 4. Webster's II New Riverside University Dictionary. Riverside Pub. Co., c1984. pp. 1-3.*

Mulligan, Jeffrey B., "Image Processing for Improved Eye-Tracking Accuracy", *Behavior Research Methods, Instruments, & Computers*, pp. 54-65, 29(1), 1997.

* cited by examiner

*Primary Examiner* — Matthew Bella
*Assistant Examiner* — Julian Brooks
(74) *Attorney, Agent, or Firm* — Marger Johnson & McCollom, P.C.

(57) ABSTRACT

An eye tracking method for determining a position of an eye or a part of an eye in an image of an image sequence by performing a comparison between said image and a reference image, said process including:
     aligning a set of images;
     computing an enhanced reference image based on a combination of said set of aligned images; and
     determining said position in said image of said image sequence by comparing said image of said image sequence and said enhanced reference image to yield a motion estimation between said reference image and said image of said sequence.

30 Claims, 4 Drawing Sheets

METHOD AND APPARATUS FOR IMAGE-BASED EYE TRACKING FOR RETINAL DIAGNOSTIC OR SURGERY DEVICE

FIELD OF THE INVENTION

The present invention relates to a method and an apparatus used in image-based tracking of eye movement or position in a retinal diagnostic/surgical device.

BACKGROUND OF THE INVENTION

Image-based tracking of eye movement or position is known to be used for several applications such as surgery and diagnostics, one example being a retinal diagnostic/surgical device. However, conventional eye tracking techniques suffer from several problems. One problem is the image quality provided by the system, e.g. the signal-to-noise ratio SNR. If the SNR is low, then the image processing techniques used for eye tracking are not as accurate as they could be. Moreover, there are problems which are due to the specific instrumentational configuration.

One such example is retinal video tracking for a Optical Coherence Tomography (OCT) device for measuring thickness and structure of the retinal layers, but other specific fields such as devices for surgery, diagnosis or monitoring of the eye can be mentioned here as well.

In case of an OCT system, the measurement beam of the OCT interferes with the fundus imaging due to fact that the illumination spectrum of the beam is close to the imaging spectrum (near IR). The effects of the OCT beam can be described as having two components:
  Saturations of the image on small areas where the beam hits the retinal surface
  Low frequency illumination changes that are caused by beam light diffusion at the retinal surface and beam light reflection from retinal surface.

Additionally image is corrupted by acquisition noise and by illumination distortions caused by the pupil size and alignment changes during the procedure.

can be applied to any device in which either a measurement scanning beam or surgical laser beam effects the retinal image used for tracking or alignment.

It is therefore an object of the present invention to provide a method and apparatus which is capable to enhance the performance of a conventional eye tracking system.

SUMMARY OF THE INVENTION

According to a first aspect of the present invention there is provided an eye tracking method for determining a position of an eye or an eye feature such as the retina in an image of an image sequence by performing a comparison between said image and a reference image, said process including:
  aligning a set of images;
  computing an enhanced reference image based on a combination of said set of aligned images; and
  determining said position in said image of said image sequence by comparing said image of said image sequence and said enhanced reference image to yield a motion estimation between said reference image and said image of said sequence.

By using an enhanced reference image it is possible to improve the overall accuracy of the eye tracking method, thereby enhancing its performance.

In case of an OCT system thereby it becomes possible to allow tracking despite the use of disturbed (real-time) images without necessitating any hardware changes to the optics or hardware to reduce the influence of the scanning beam due to the use of an enhanced reference image for comparison with the real-time images.

A set of images taken in advance may be aligned to the same retinal position and then combined by averaging the aligned set of images to generate the enhanced reference image. This enhanced reference image may then be used for position determination and tracking in combination with a diagnosis and/or surgical device The diagnosis and/or surgical device in one embodiment may be one of the following:
  an OCT apparatus;
  a refractive surgery device.

According to one embodiment there is performed an OCT spot trace rectification to eliminate a saturated OCT spot trace from an image in said sequence by replacing the saturated area by an interpolation or an average intensity in a corresponding area of unsaturated images compensating illumination variations using one or more suitable filters. This reduces the disturbing effect of the OCT spot.

According to an embodiment a motion estimation comprises:
  performing a global motion estimation between said reference image and said image of said sequence; and
  performing a motion estimation based on parts or landmarks of said reference image and said image of said image sequence. This two-step mechanism yields a better accuracy and is less prone to disturbing effects.

In one embodiment said global motion estimation is refined by said motion estimation based on parts or landmarks. They may be selected by the user or they may be automatically selected.

In one embodiment the enhanced reference image is used for one or more of the following:
  OCT spot rectification;
  deriving a spectrally matched filter for selecting one or more retina spectrum components having the highest SNR ratio.

In one embodiment the method further comprises:
  aligning image sequences taken at different periods of time by aligning an enhanced reference corresponding to one of said sequences with a reference image or an enhanced reference image corresponding to said second sequence. This enables an inter-session alignment necessary for a long-tem diagnosis.

According to one embodiment there is provided a method of enhancing the video display of an image of an eye or a portion of an eye, said method comprising:
  aligning a sequence of images which are preceding an actual image of said video stream with respect to said actual image;
  combining the resulting aligned set of images into an enhanced image to be used as a basis for an enhanced actual image of said video stream. Thereby the quality of the video stream may be enhanced.

According to one embodiment the method comprises aligning said images of said preceding sequence based on eye tracking information, and for the eye tracking the enhanced reference image may be used.

According to one embodiment there is provided a method for operating a diagnostic or surgical device based on eye tracking, said method comprising:
  determining whether an anomaly is detected during said eye tracking;

if an anomaly is detected during said eye tracking, putting said diagnostic or surgical device in a HOLD mode. This enables the system to avoid the negative influence of anomalies in eye motion such as saccades or links.

According to one embodiment an anomaly is one or more of the following:
- a change in image quality beyond a certain threshold;
- a fast movement of the eye the speed of which is beyond a certain threshold;
- a blurring of the image used for eye tracking;
- a blurring of the image used for eye tracking in combination with a fast movement;
- a cumulated difference between subsequent tracking images lying beyond a certain threshold.

In one embodiment the method may further comprise:
determining those locations where the operation of the surgical or diagnostic device did nod lead to a correct result;
re-running the operation of said surgical or diagnostic device for said determined locations.

Further embodiments comprise systems and apparatuses which implement the methods according to embodiments of the invention.

DETAILED DESCRIPTION

A first embodiment of the present invention will now be described in connection with FIG. 1. A camera (e.g. a CCD camera) 110 takes video images of an eye 100, and the images are fed to a computer 120. Such an arrangement is equal to a classical eye tracking system and it may also be applied to the present invention. In the conventional eye tracking system, based on the images captured the computer 120 "tracks" the eye movement, e.g. by comparing the position of some "landmarks" in the momentary image with the position in the previous image to thereby "track" the movement of the eye. Based on the tracked actual position a feedback signal may be determined which then is used to carry out a position compensation at a surgical or diagnostic device (not shown in FIG. 1).

Figure 2:
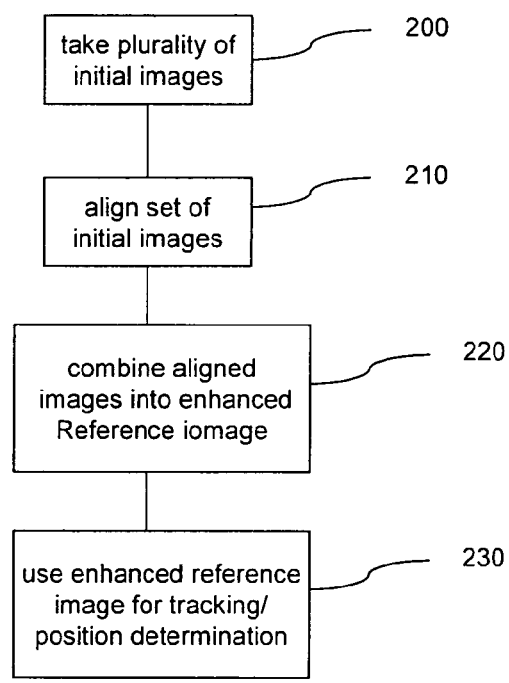
FIG. 2 schematically illustrates a method according to an embodiment of the invention.

In order to track the movement of the eye or to determine the position of the eye an instantaneous image of the eye is compared with some reference image. According the present embodiment this reference image is derived by combining a plurality of images into an enhanced reference image. This is now explained in somewhat more detail in connection with FIG. 2.

In operation 200 a plurality of "initial images" is taken, e.g. by capturing an image sequence before the actual tracking starts. E.g. for 0.5 seconds before the actual tracking the camera captures an image sequence, this yields a set of "initial images" based on which the enhanced reference image then will be derived.

In operation 210 the initial images then are aligned with respect to their position. This can be done using some standard motion estimation method for each of the initial images and then aligning them based on the result.

In operation 220 the thus aligned initial images then are combined into an enhanced reference image, e.g. by averaging the initial images into a single image which then has an enhanced SNR.

In operation 230 the enhanced reference image then is used for tracking or position measurement, e.g. by comparing the position of an instantaneous image with the enhanced reference image.

According to one embodiment the eye tracking consists of two major elements which are as follows:
A. Image set alignment
B. Image sequence alignment The image set alignment takes a set of (e.g.) retinal images as input and produces an enhanced (retinal) image as output by combining the information in the image set. The image set alignment in one embodiment is done before the actual tracking and does not bare real-time constraints so that the method used to implement in a manner oriented to maximize the quality of the result.

The image sequence alignment makes use of the enhanced retinal image formerly produced, in order to compare a sequence of new retinal images to the mentioned enhanced retinal image for determination of eye position/eye movement of to perform eye tracking. The image sequence alignment has real-time constraints (due to the continuous input of real-time instantaneous images) and according to one embodiment is oriented for an optimal compromise between motion determination quality and computational effort.

In the following another embodiment will be described in somewhat more detail which relates to an application in the field of optical coherence tomography (OCT). An OCT system works similar to an ultrasound imaging device except that instead of ultrasound it uses infrared (IR) light which is emitted as OCT beam, reflected by the retina and then based on the reflected light and image processing methods a diagnostic image is obtained. Such systems are well known to a person skilled in the art and are therefore not described any further herein.

In both set and sequence alignment in an OCT system a main problem is that of the adverse effects of OCT beam. A preprocessing method that compensates for these effects is described in the following. According to one embodiment this method comprises the acquisition of the image set used for deriving the enhanced reference image, furthermore it comprises an illumination normalization and an OCT spot trace rectification.

At first the preprocessing method will be described. Later then the image set/sequence alignment will be described.

The preprocessing method in one embodiment consists of following sub-steps:
1. Select a small set (or subset) of images at the beginning of the procedure
2. Preprocess each image in order to reduce the illumination distortion effects
3. Preprocess each image to rectify the OCT spot trace (saturated pixels)
4. Align the image set with respect to each other and average the set temporary to reduce the effect of acquisition noise as well as other residual distortions The subset of images is acquired previous to the beginning of the scan mode—in the scan alignment mode. In one embodiment approx. 0.5 seconds of live video stream are taken that are buffered into memory and processed afterwards. If images during this period are suffering from bad quality (very low contrast or large saturated areas) they are rejected.

Then the preprocessing proceeds with an illumination normalization. The illumination normalization in one embodiment is performed as a combination of homomorphic and high pass filtering. Namely, the signal pixels are altered by a multiplicative or/and additive influence of the illumination strength. If light is reflected from retina, the effect is multiplicative (i.e. contrast increases). If light is diffused by retina from punctual sources, the effect is additive (i.e. brightness increases).

In practice both effects appear. In the pupil vignetted areas the effect is mainly multiplicative, while close to the beam trace the effect is more additive. An illumination normalization attempts to reduce these effects, and in one embodiment the method can operate as follows:

1. Perform a low pass filtering with a large kernel (e.g. 10-20 pixels). The result represents the illumination variation Ilum. Standard methods known to the expert can be used to perform the low pass filtering.
2. Correct each pixels after the relation:

$$Im(x,y)=\text{alpha}*(m(x,y)/Ilum(x,y))+(1-\text{alpha})*(Im(x,y)-Ilum(x,y))$$

The parameter alpha controls the weight on multiplicative/additive correction and varies with the position in the image. More precisely the alpha value is depending on the intensity of pixels in Im(x,y) according to a predefined function. Typically for dark pixels it will chosen to be closer to 1, while for pixels close to the saturation it will be chosen to be closer to 0. Both additive and multiplicative image correction methods are well known in the art. The combination of the two models is also straightforward to the skilled person. Details can be found in any image processing textbook, e.g: Anil K. Jain, *Fundamentals of Digital Image Processing*, Prentice Hall 1988. (Note: for simplicity, the given equation omits certain fixed offset/scaling factors used for making the multiplicative/additive images comparable)

It should be noted that the low pass filter on the above will cause ringing in the vicinity of the OCT beam spot, because the illumination varies very abruptly in those areas.

The treatment of saturated pixels requires therefore a different compensation (or "correction") approach. In one embodiment the saturation effects can be dealt with using a method which comprises the following steps:

1. The OCT spot trace is first identified by performing an image thresholding to detect the very bright pixels.
2. The binary image is blurred with a kernel identical to the one used at the illumination normalization step. All pixels that are non zero in this mask image, represent non-valid pixels (corresponding to saturated pixels). The blurring takes into account that the thresholding may "overlook" some pixels at the edge of saturated areas which in fact should also be considered as needing compensation. For the blurring any standard "blurring method" known to experts in the field of image processing may be used.
3. The entire set of illumination normalized images is averaged over time, taking care that non-valid pixels are ignored. The non-valid pixels are treated differently as described in the following.
4. Each image is rectified in the non-valid pixels as an alpha-blending between the image and the average image. The alpha factor is represented by the mask image computed during the illumination normalization process.

After illumination normalization the preprocessing according to one embodiment is completed and the method may now proceed with aligning the initial set or subset of images which has been preprocessed.

Direct image to image alignment is difficult in low SNR images. According to an embodiment of the invention therefore an enhanced reference image is derived to which then is used for eye position determination. This improves SNR and yields better accuracy.

In detail, according to one embodiment alignment of the initial set for obtaining the enhanced reference image in order to improve SNR operates as follows. At first one can perform a large set of measurements that are redundant and proceed by solving an over determined system of equations. Given n images, such approach would require to compute the displacement between each pair of images (1, 2) (1,3) . . . (1,n), (2,3), (2,4) . . . (2,n) . . . (n−1,n). This leads to n(n+1)/2 image pairs comparisons to obtain the displacements of the individual images which then may be aligned and added or averaged. However, in terms of time necessary to perform the calculation this is a kind of "brute force" method which in principle works but which can—according to further embodiments—be replaced by more efficient calculation methods.

For example, it can be noticed that in case of linear operators (such as correlation family), the order of operations can be inversed, namely one can first add k images and than compute the displacement, instead of computing k displacements and then adding results. This approach works as long as the k images are not moving much with respect to each other.

However, eye movement research shows the following facts:

motion during short fixations are small
fixations durations is of at least 100 ms
saccades/flicks during fixations are less than 30 ms
saccades/flicks during fixations are low frequency <3/sec Based on this according to one embodiment can proceed as follows:

1. Divide an initial set of 32 images in 4 subsets of 8 images. Each subset represents a time span of 128 ms.
2. Average the each subset to obtain an average image per subset.
3. Measure the displacement of an image with respect to the 3 average images from the subsets that it does not belong.
4. Take the median of the 3 measurements as the actual displacement
5. Based on the results obtained shift each image so that the set is now aligned, and then average all 32 images to obtain the final reference enhanced image.

The particular numbers in the foregoing example are to be understood as being just informative examples, the method can be applied with any number of images/subsets, etc.

Figure 3:
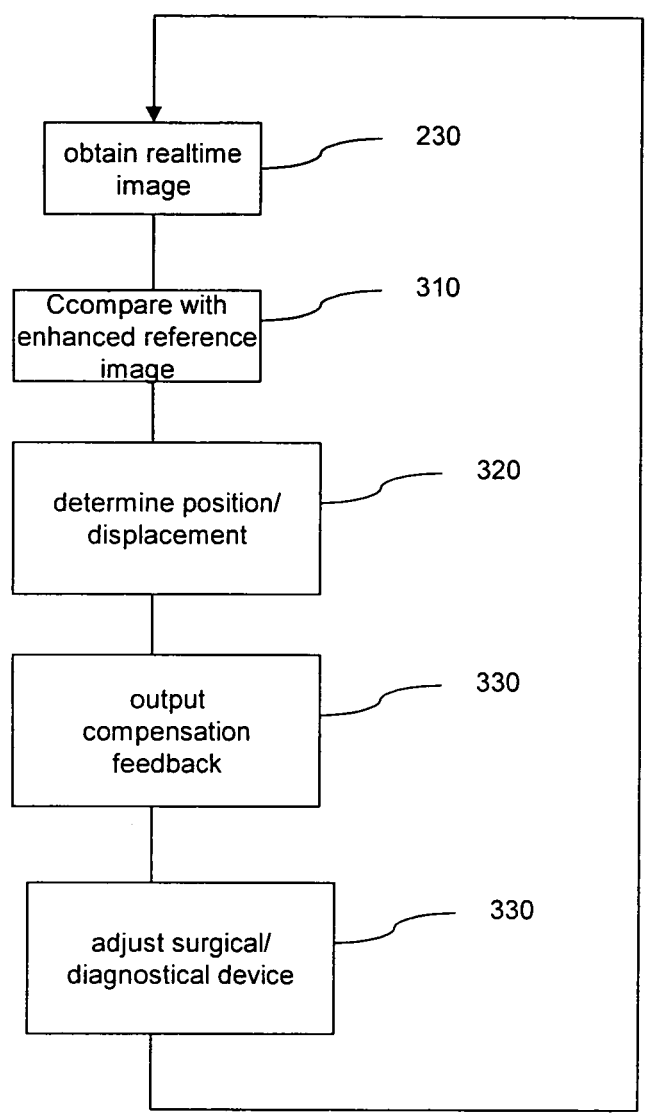
FIG. 3 schematically illustrates a method according to a further embodiment of the invention.

After having obtained the enhanced reference image as described before this enhanced reference image can be used for determining eye position or eye movement or eye tracking. An example of the use of the enhanced reference image could be in connection with a surgical/diagnostic device which needs a feedback for compensating the movement of the eye, typically in real-time. The operation of such a system is schematically illustrated by the flowchart shown in FIG. 3.

Figure 1:
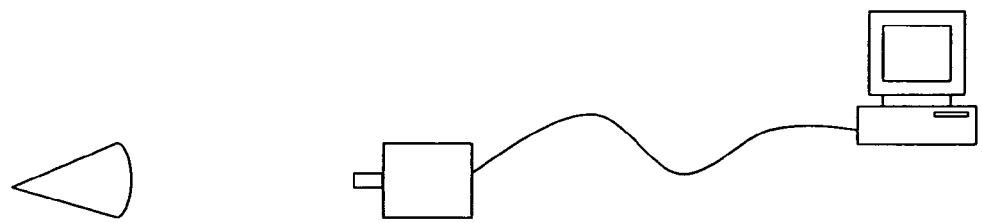
FIG. 1 schematically illustrates a configuration for implementing an embodiment of the present invention.

In operation 300 a real-time image of the eye (or a part of it, or some of its parts) is obtained, e.g. by use of a system schematically shown in FIG. 1. The thus obtained image is then compared in operation 310 with the enhanced reference image, e.g. by using any standard method to determine the motion or displacement between the two images. Such methods for motion estimation are well known to the expert and are therefore here not described in any more detail. In operation 320 then the actual displacement is determined by using the motion estimation method applied in operation 310. This then yields the actual position (or the displacement with respect to the reference image) of the image taken in operation 300. Based on the displacement in operation 330 then a compensation feedback value is determined, this may e.g. be a signal to be used for controlling the surgical/diagnostic device or its components such that the eye movement is compensated. In operation 340 then based on this feedback the actual compensation is performed in the surgical/diagnostic device. Thereafter the procedure may continue by acquiring the next image by returning to operation 300.

Image sequence alignment (or position measurement) differs from image set alignment by the fact that the image data is presented in a temporal sequence rather than simultaneously. That means that aligning an image can be done only with the information gathered up to the point of measurement. Sequence alignment is the basis of any real-time video tracking.

The sequence alignment method of the present embodiment makes use of the reference enhanced image obtained as described before. According to a particular embodiment the enhanced reference image is used in sequence alignment or real-time position determination for one or more of the following purposes:
1. For OCT spot rectification. Similar to the OCT spot rectification method described before in connection with the alignment of the initial set of images the OCT rectification can also be performed for the real-time images obtained during an OCT scan. The saturated pixels then are replaced by pixel values which are based on the values of the enhanced reference image for these pixels.
2. For deriving a spectrally matched filter that selects the retinal spectrum components with the highest SNR ratio. Based on the enhanced reference image an analysis can be made which spectral components have the highest SNR. These spectral components then may also be used for the actual sequence alignment during real-time data acquisition.
3. For detection of useful landmarks such as retinal vessels, optical nerve, macular exudates. The thus detected landmarks which have been detected in the enhanced reference image either manually or automatically may then be used for position determination during sequence alignment.
4. For performing matching techniques (such as phase correlation, cross correlation, entropy maximization, etc) between reference image and the currently measured image. These methods then actually yield the displacement which then may be used to generate a compensation feedback at the diagnostic or surgical device. or The matching techniques could be global at the level of entire image or local, at the level of landmarks as detected at step 3.

In all mentioned points, the higher quality of the enhanced reference image is increasing performance over the use of any particular image of the sequence.

Figure 4:
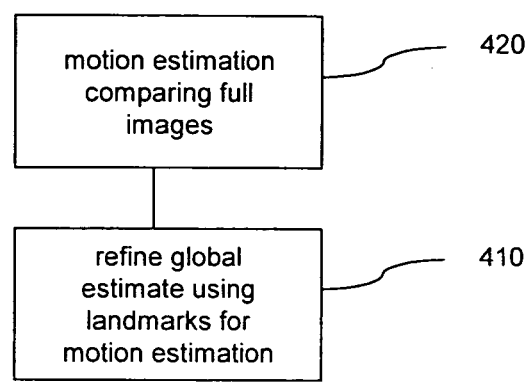
FIG. 4 schematically illustrates a motion estimation method according to a further embodiment of the invention.

A specific embodiment for determining the position of the eye is now described in the following. Basically the method comprises two major elements, a first being a motion estimation at a global level, and the result of this global motion estimation being refined by using a local motion estimation by using one or more local landmarks detected in the reference image. This is schematically illustrated in FIG. 4, where operation 400 shows a global motion estimation based on the whole actual image and the whole reference image. The resulting estimate suffers from inaccuracies which may result from multiple motions or from occlusion/saturation effects due to the OCT beam. This estimate is then in operation 410 refined by the local motion estimation which may be based on one or more landmarks which have been selected in the enhanced reference image.

In somewhat more detail according to a specific embodiment this may be described as follows.
1. a global level estimation is performed using the entire information available. This estimation is performed by matched phase correlation. Matched phase correlation is a standard method for motion estimation and well known to the skilled person. It is yields a set of peaks at positions corresponding to possible displacements between the actual and the reference image. The global estimation provides a small set of possible locations of the retina (1-5 locations) corresponding to respective possible eye movements. The global step provides robustness over illumination changes, noise, etc.
2. Then there is performed a local level estimation using a set of landmarks detected in the reference image. This helps to decide which of the location candidates delivered by step 1 is the correct one. The local estimation provides flexibility to adjust over objects occlusions and multiple motions that global step cannot resolve.

In the following there will be described a further embodiment of the present invention which relates to an OCT device providing an OCT image of the retina. This device makes use of a retina tracker which provides real-time information about the retina x/y displacements relative to the reference image. The OCT scanning system adjusts the scan pattern to take into account the changes in retina position, so that the scanning path follows the intended trajectory.

Figure 5:
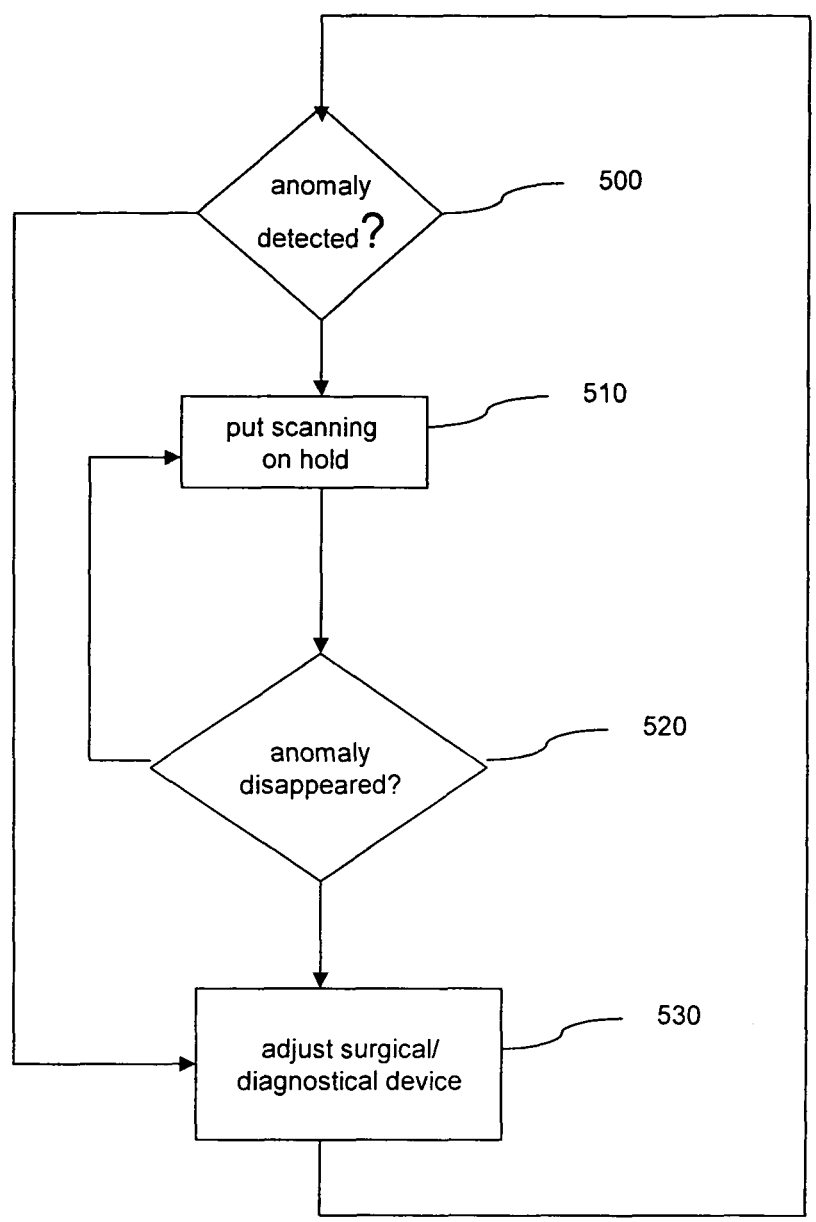
FIG. 5 schematically illustrates a method according to a further embodiment of the invention.

However, standard video based eye trackers (<=60 Hz) are too slow to correctly compensate the fast movements of the retina that are typical to saccades. Also, retinal tracking can be temporary unavailable due to blinks, large pupil occlusions, etc. In order to take into account and to compensate those effects the following two methods of operation are performed in this embodiment.
I. The diagnostic/surgery device, and in one particular embodiment the OCT scan beam is put on hold if an anomaly is detected in the image sequence used for tracking. The retinal tracking system detects anomalies in tracking such as saccades, blinks, etc. (see operation 500 in FIG. 5). This can be done using certain suitable criteria. E.g. a sudden loss in image quality (a decrease of a quality factor below a certain threshold) may be representative of a blink. On the other hand, a blurring of the image in connection with a fast movement can be considered as being representative of a saccade. Using such kind of criteria it can be determined whether an anomaly occurred which may negatively influence the performance of the tracking and/or the performance of the surgical/diagnostic device. In our specific embodiment the device is an OCT device, and if an anomaly is detected the retinal tracking system in operation 510 delivers a HOLD signal to the OCT scanning system. When the HOLD signal is active (as long as operation 520 in FIG. 5 does not lead to an affirmative answer), the OCT scanning system stops the scanning pattern program. When in operation 520 it is determined that the anomaly is not present anymore, then the HOLD signal becomes inactive and the scan continues. In this way, the transient parts are avoided as long as they are detected by the retinal tracking system.

II. A further operation method may be employed additionally or alternatively. In the present embodiment it is employed additionally, therefore the system maintains all parts described at point 1. Additionally, based on further data obtained by the retinal tracking system, such as the future trajectory of the retina and potentially by the OCT scan data, certain scan parts can be retrospectively considered invalid. The invalidation is meant to occur mainly in two situations:

a. A detection of a saccade will allow eliminating the samples from the saccade start, which could not be eliminated by the first method. The saccades are detected by means of retinal velocity, as a sequence of 3-5 high-speed samples. By fitting a predefined parameterized function (such as a sigmoid or polynomial) to the data samples, a more precise start/end of the saccade can be obtained b. A detection of accidental tracking errors, that appears as a disrupter in the trajectory of the retina. These outlier measurements are detected by means of statistic filtering. Principally, this comes to evaluating the probability that a certain position value occurs in a given trajectory context. The probabilities are computed off line based on a large dataset of common eye dynamics. The measurements with low probability are rejected The OCT scanning system then reprograms the reacquisition of those invalid parts on a second pass. Third pass and so on may be employed until the desired result is achieved. This method, may provide more robustness as the decision on where the scanning was inadequate is based on more data.

In the following a further embodiment of the present invention will be described where the invention is applied in an OCT device for retinal imaging. The diagnosis of a retinal disease usually requires monitoring changes in the retina over a certain period of time. This implies that multiple OCT scans are required to be performed at various intervals on the same patient in the same location of the retina.

In order to reliably monitor significant changes, it is of high importance to be able to ensure that different scan sessions are performed on same retinal location. The current inter-sessions alignment procedure is very approximate as the low quality of IR fundus video does not allow the doctor to make precise adjustments of the scan placement. The red—free image snapshot capability cannot be used before the diagnosis—only after the diagnosis—as the bright green light constricts the pupil. It is, however, desirable to have the OCT system properly aligned before the scan, and for that the red-free image cannot be used because of its effects on the pupil which would disturb the subsequent diagnostic measurement.

The enhanced reference image, however, provides enough visual quality to be used either in a manual or automatic way in order to perform the alignment of the scan with respect to another surgery.

According to an embodiment the system is able to perform the following automatic alignments:

1. Enhanced IR to Enhanced IR
2. Enhanced IR to Red Free

The same types of alignment can be performed manually by the doctor who is provided with a software tool that allows free adjustments of Enhanced IR image in order to highlight various features (retinal vessels, optical nerve head, exudates, etc.). In case of automatic alignment some motion estimation algorithm is used and based on its result the alignment is then performed.

The use of the Enhanced Reference Image leads to several benefits:

It can be used prior to the start of scanning as opposed to the Red-Free image

It offers the required visual quality that allows the operator to validate/perform the alignment It allows robust automatic alignment with enhanced IR images or Red-Free images from other sessions In the following a further embodiment of the invention will be described which relates to the enhancement of the quality of a video image stream. The raw video stream is having a poor SNR that makes typical corrections such as brightness/contrast adjustment ineffective.

The present embodiment makes use of the tracking information in order to increase the SNR of each video frame. Subsequently, other enhancement techniques (brightness/contrast adjustment, sharpening, shadow correction, etc.) may be applied to provide a real time enhanced display.

The method consists of following steps:

For each image in the video stream

1. Take the last N images (N=10-25) and align them with respect to the current image, based on the tracking information. The alignment is performed here by shifting images in x and y coordinates. Other type of alignment, such as rotation and scaling or combinations of those can also be employed if required.
2. Replace each pixel value in the display image by the average (or weighted average) of pixel values in the last N aligned images. The above two steps can be expressed by the relation:

$$Dspl^n(x,y)Im^n(x,y)+Im^{n-1}(x-dx^{n-1},y-dy^{n-1})+\ldots Im^{n-N}(x-dx^{n-N},y-dy^{n-N}),$$

where n represents the n-th image of the video stream, $dx^i/dy^i$ represents the shift in x/y of the image i relative to the image n 3. Apply the desired enhancement techniques to image Displ and send it to the display output With the method described before the quality of each individual video image and thereby of the whole video stream can be increased.

The skilled person will understand that the methods, apparatuses and systems according to embodiments of the invention as described hereinbefore may be implemented by a configuration comprising a standard video camera, and a standard computer as schematically illustrated in FIG. 1. The computer may be equipped with some standard software for video capturing, and as far as the foregoing description and the claims relate to modules or components implementing the invention the skilled person will readily understand that they may be implemented either in hardware or in software in connection with the basic configuration shown in FIG. 1. Apart from video eye tracking systems the invention may be applied to any eye tracking system that outputs eye position data. Based on the foregoing description the skilled person will be readily able to adapt the system shown in FIG. 1 by suitable programming of the computer and its components to perform the functions described in connection with the embodiments of the present invention.

It is further to be understood that the foregoing embodiments are described as exemplary embodiments only, and that modifications to these embodiments are possible to the skilled person and should therefore be considered as lying within the scope of the invention. E.g. in addition to an OCT device the invention may be applied to any surgical or diagnostic device. Moreover, apart from the area of surgical and diagnostic devices the present invention may be applied in the field of eye tracking and in eye tracking devices in general.

What is claimed is:

1. An eye tracking method for determining a position of an eye or a part of an eye in an image of an image sequence by performing a comparison between said image and a reference image, said process including:
    aligning a set of images of the eye or the part of the eye to a same retinal position by shifting one or more images of the set of images within one or more respective image planes;
    computing an enhanced reference image based on a combination of said set of aligned images; and
    determining said position of the eye or the part of the eye in said image of said image sequence by comparing said image of said image sequence and said enhanced reference image to yield a motion estimation between said reference image and said image of said sequence.

2. The method of claim 1, further comprising:
    combining the aligned set of images by averaging the aligned set of images to generate the enhanced reference image.

3. The method of claim 1, further comprising:
    using said retina position determined in said image sequence for tracking in connection with a diagnosis and/or surgical device.

4. The method of claim 3, wherein said diagnosis and/or surgical device is one of the following:
    an OCT apparatus;
    a refractive surgery device.

5. The method of claim 1, further comprising the following:
    performing OCT spot trace rectification to eliminate a saturated OCT spot trace from an image in said sequence by replacing the saturated area by an interpolation in a corresponding area of unsaturated images and compensating illumination variations using one or more suitable filters.

6. The method of claim 1, comprising:
    performing a global motion estimation between said reference image and said image of said sequence.

7. The method of claim 6, wherein
    said global motion estimation is refined by performing a motion estimation based on parts or landmarks of said reference image and said image of said image sequence.

8. The method of claim 1, wherein said enhanced reference image is used for
    OCT spot rectification.

9. The method of claim 1 further comprising:
    aligning image sequences taken at different periods of time by aligning an enhanced reference corresponding to one of said sequences with a reference image or an enhanced reference image corresponding to said second sequence.

10. The method of claim 9, wherein said reference image corresponding to said second sequence is a red-free image.

11. The eye tracking method of claim 1 in which aligning a set of images to the same retinal position comprises motion estimation.

12. The method of claim 1, further comprising:
    using said retina position determined in said image sequence for positional compensation in connection with a diagnosis and/or surgical device.

13. The method of claim 1, further comprising the following:
    performing OCT spot trace rectification to eliminate a saturated OCT spot trace from an image in said sequence by replacing the saturated area by an average intensity in a corresponding area of unsaturated images and compensating illumination variations using one or more suitable filters.

14. The method of claim 5 in which the one or more suitable filters comprise spatial spectral filters.

15. The method of claim 13 in which the one or more suitable filters comprise spatial spectral filters.

16. The method of claim 1, comprising:
    performing a motion estimation based on parts or landmarks of said reference image and said image of said image sequence.

17. The method of claim 1, wherein said enhanced reference image is used for
    deriving a spectrally matched filter for selecting one or more retina spectrum components having the highest SNR ratio.

18. An eye tracking system for determining a position of an eye or a part of an eye in an image of an image sequence by performing a comparison between said image and a reference image, said system including:
    a computer comprising:
        a module for aligning a set of images by re-positioning individual images in the set of images to a same retinal position;
        a module for computing an enhanced reference image based on a combination of said set of aligned images;
        a module for determining said position in said image of said image sequence by comparing said image of said image sequence and said enhanced reference image to yield a motion estimation between said enhanced reference image and said image of said sequence; and
        a module for performing OCT spot trace rectification to eliminate a saturated OCT spot trace from an image in said sequence by replacing the saturated area by an interpolation in a corresponding area of unsaturated images or an average intensity in a corresponding area of unsaturated images.

19. The system of claim 18, wherein the computer further comprises:
    a module for aligning said set of images which are taken before said image sequence to the same retinal position;
    a module for combining the aligned set of images by averaging the aligned set of images to generate the enhanced reference image.

20. The system of claim 18, wherein the computer further comprises:
    a module for using said retina position determined in said image sequence for tracking in connection with a diagnosis or surgical device.

21. The system of claim 20, wherein said diagnosis or surgical device is one of the following:
    an OCT apparatus;
    a refractive surgery device.

22. The system of claim 18, wherein the computer further comprises
    a module for compensating illumination variations using one or more suitable filters.

23. The system of claim 18, wherein the computer further comprises one or more of the following:
    a module for performing a global motion estimation between said reference image and said image of said sequence;

a module for performing a motion estimation based on parts or landmarks of said reference image and said image of said image sequence.

24. The system of claim 23, wherein said global motion estimation is refined by said motion estimation based on parts or landmarks.

25. The system of claim 18, wherein said enhanced reference image is used for the following:

OCT spot rectification or deriving a spectrally matched filter for selecting one or more retina spectrum components having the highest SNR ratio.

26. The system of claim 18, wherein the computer further comprises:

a module for aligning image sequences taken at different periods of time by aligning an enhanced reference corresponding to one of said sequences with a reference image or an enhanced reference image corresponding to said second sequence.

27. The system of claim 26, wherein said reference image corresponding to said second sequence is a red-free image.

28. The system of claim 18, further comprising:

a module for using said retina position determined in said image sequence for positional compensation in connection with a diagnosis or surgical device.

29. The system of claim 22 in which the one or more suitable filters comprise spatial spectral filters.

30. A computer program product recorded on a non-transitory computer-readable medium, the computer program product comprising computer instructions that, when executed causes a computer to:

align a set of images of an eye or a part of an eye to a same retinal position by shifting one or more images of the set of images within one or more respective image planes;

compute an enhanced reference image based on a combination of said set of aligned images;

after computing said enhanced reference image, obtain an image sequence, said image sequence including an image of the eye or the part of the eye; and after obtaining said image sequence, determine a position of the eye or the part of the eye in said image of said image sequence by comparing said image of said image sequence and said enhanced reference image to yield a motion estimation between said reference image and said image of said image sequence.

* * * * *